(12) United States Patent
Hoelzer et al.

(10) Patent No.: US 12,646,169 B2
(45) Date of Patent: Jun. 2, 2026

(54) METHOD AND DATA PROCESSING SYSTEM FOR PROVIDING RADIOLOGICAL VISUALIZATION DATA

(71) Applicant: Siemens Healthineers AG, Forchheim (DE)

(72) Inventors: Philipp Hoelzer, Tokyo (JP); Sebastian Schmidt, Weisendorf (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 327 days.

(21) Appl. No.: 18/459,758

(22) Filed: Sep. 1, 2023

(65) Prior Publication Data

US 2024/0078667 A1     Mar. 7, 2024

(30) Foreign Application Priority Data

Sep. 2, 2022     (DE) ..................... 10 2022 209 173.6

(51) Int. Cl.
 *G06T 7/00*          (2017.01)
 *G06T 7/11*          (2017.01)
 *G16H 30/40*       (2018.01)

(52) U.S. Cl.
 CPC .............. *G06T 7/0012* (2013.01); *G06T 7/11* (2017.01); *G16H 30/40* (2018.01); *G06T 2207/10124* (2013.01)

(58) Field of Classification Search
 None
 See application file for complete search history.

(56) References Cited

U.S. PATENT DOCUMENTS

| | | | |
|---|---|---|---|
| 8,149,238 B2 * | 4/2012 | Buyanovskiy | ........ G06T 17/005 |
| | | | 345/426 |
| 9,042,617 B1 * | 5/2015 | Reicher | .................. H04L 67/10 |
| | | | 382/128 |
| 2003/0097055 A1 | 5/2003 | Yanof et al. | |

(Continued)

FOREIGN PATENT DOCUMENTS

| | | | |
|---|---|---|---|
| CA | 2295689 C | * 12/2003 | ............. H04N 19/17 |
| DE | 102016219488 A1 | 4/2018 | |
| DE | 102019210473 A1 | 1/2021 | |

OTHER PUBLICATIONS

Dyer et al; Robustness of an Artificial Intelligence Solution for Diagnosis of Normal Chest X-Rays; Aug. 31, 2022.*

(Continued)

*Primary Examiner* — Fan Zhang

(74) *Attorney, Agent, or Firm* — Harness, Dickey & Pierce, P.L.C.

(57) ABSTRACT

One or more example embodiments of the present invention relates to a computer-implemented method for providing radiological visualization data. The method includes receiving radiological imaging data which relates to an examination region, calculating confidence data based on the radiological imaging data, the confidence data relating to a confidence score with which an abnormality of the examination region can be automatically excluded, calculating the radiological visualization data which relates to the examination region, wherein a data reduction of the radiological visualization data relative to the radiological imaging data is effected as a function of the confidence data, and providing the radiological visualization data.

17 Claims, 4 Drawing Sheets

(56) References Cited

U.S. PATENT DOCUMENTS

| | | | |
|---|---|---|---|
| 2009/0132916 A1* | 5/2009 | Filatov ................... | G16H 40/63 |
| | | | 715/700 |
| 2016/0364539 A1* | 12/2016 | Reicher ................. | G16H 20/10 |
| 2018/0101644 A1 | 4/2018 | Hammes et al. | |
| 2021/0019882 A1 | 1/2021 | Hofmann et al. | |
| 2021/0374948 A1 | 12/2021 | Jung | |
| 2021/0375434 A1 | 12/2021 | Kawanaka | |
| 2022/0225954 A1* | 7/2022 | Juergens .............. | A61B 6/5205 |

OTHER PUBLICATIONS

Wang et al; Dual Windows Are Significant: Learning from Mediastinal Window and Focusing on Lung Window; Jun. 8, 2022.*

McCollough et al; Dual- and Multi-Energy CT: Principles, Technical Approaches, and Clinical Applications; Nov. 12, 2014.*

Ng et al; Effect of Sampling Frequency onPerfusion Values in Perfusion CTof Lung Tumors; Feb. 1, 2012.*

* cited by examiner

US 12,646,169 B2

1

METHOD AND DATA PROCESSING SYSTEM FOR PROVIDING RADIOLOGICAL VISUALIZATION DATA

CROSS-REFERENCE TO RELATED APPLICATION(S)

The present application claims priority under 35 U.S.C. § 119 to German Patent Application No. 10 2022 209 173.6, filed Sep. 2, 2022, the entire contents of which are incorporated herein by reference.

RELATED ART

The application of artificial intelligence algorithms has the potential to automate partial aspects of the evaluation of radiological image data. It is thereby possible for example to increase the diagnostic accuracy and/or to improve the consistency of the evaluation. In particular if the artificial intelligence arrives at a result according to which an abnormality is not present, it might be necessary for a doctor to check the result.

SUMMARY

Such visual verification of the absence of an abnormality can be very time consuming for the radiology staff, particularly if all of the image data that has been analyzed by the artificial intelligence has to be assessed.

One or more example embodiments provides radiological visualization data which has been data-reduced in comparison with conventional radiological visualization data, in order to reduce the time that is required to visually check the radiological visualization data for the absence of an abnormality.

BRIEF DESCRIPTION OF THE DRAWINGS

Example embodiments of the present invention are explained below on the basis of exemplary embodiments with reference to the appended figures. The representation in the figures is schematic, greatly simplified and not necessarily in proportion.

2

Figures 6, 7:
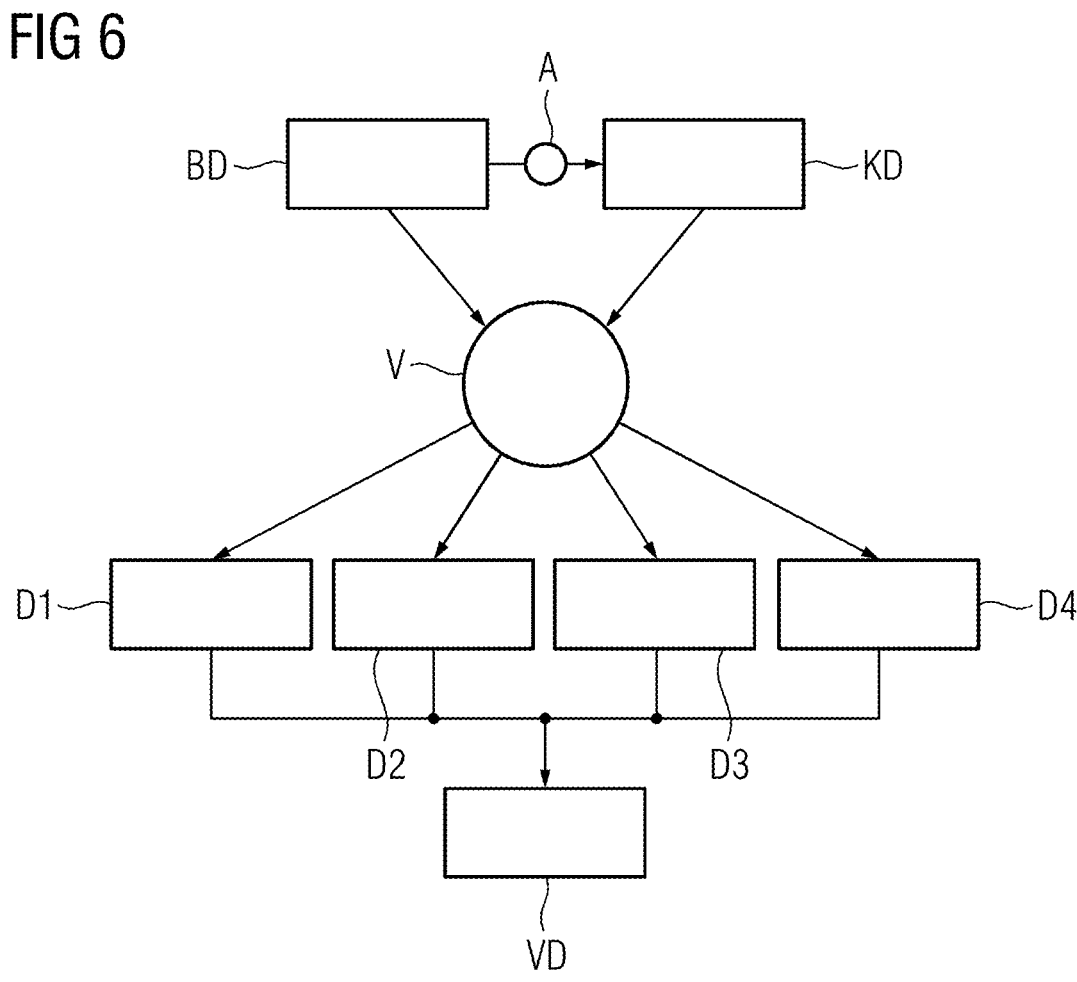
FIG. 6 shows an exemplary data flow diagram of the method for providing radiological visualization data according to one or more example embodiments.

FIG. 7 shows a data processing system according to one or more example embodiments.

DETAILED DESCRIPTION

One or more example embodiments of the present invention relates to a computer-implemented method for providing radiological visualization data, said method comprising:
   receiving radiological imaging data which relates to an examination region,
   calculating confidence data on the basis of the radiological imaging data, said confidence data relating to a confidence score with which an abnormality of the examination region can be automatically excluded, in particular is automatically excluded,
   calculating the radiological visualization data which relates to the examination region, a data reduction of the radiological visualization data relative to the radiological imaging data being effected as a function of the confidence data,
   providing the radiological visualization data.

The radiological imaging data can be for example generated via a medical imaging device and/or based on a radiological imaging examination of the examination region. In particular, the radiological imaging examination of the examination region can be performed via the medical imaging device, the radiological imaging data being generated via the medical imaging device.

The radiological imaging data can be selected for example from the group of imaging data comprising x-ray imaging data, C-arm x-ray imaging data, computed tomography imaging data (CT imaging data), molecular imaging data (MI imaging data), single-photon emission computed tomography imaging data (SPECT imaging data), positron emission tomography imaging data (PET imaging data), magnetic resonance tomography imaging data (MR imaging data), ultrasound imaging data and combinations thereof, in particular PET-CT imaging data and PET-MR imaging data.

The calculation of the confidence data can be effected for example by applying an abnormality detection algorithm to the radiological imaging data. In particular, provision can be made for the abnormality detection algorithm to identify one or more types of abnormalities and/or support a decision concerning the presence of an abnormality of the examination region. In particular, provision can be made for the abnormality detection algorithm to allow for all types of abnormalities that are to be evaluated and are relevant for a specific medical examination ("case-level rule-out"). For this purpose, the abnormality detection algorithm can comprise for example a plurality of evaluation-specific algorithms.

The abnormality detection algorithm can be for example specialized in respect of an abnormality of the examination region whose identification requires a high resolution, in particular in respect of an abnormality which is diffuse and/or has very fine features. The abnormality of the examination region can be for example a lesion. In particular, the lesion can be small and/or focal.

In particular, provision can be made for the abnormality detection algorithm to be applied to the radiological imaging data in order to exclude the abnormality of the examination region automatically, and/or such that in this way the abnormality of the examination region is automatically excluded, in particular automatically excluded with the confidence score.

A confidence score with which the abnormality of the examination region can be automatically excluded can be in particular a measure of how reliably the abnormality of the examination region can be automatically excluded. The confidence score with which the abnormality of the examination region can be automatically excluded can be based in particular on a probability that the automatically excluded abnormality of the examination region is truly not present, and/or indicate a probability that the automatically excluded abnormality of the examination region is truly not present.

The confidence score with which the abnormality of the examination region can be automatically excluded can be in particular a confidence score with which the abnormality of the examination region can be automatically excluded by the abnormality detection algorithm, in particular can be automatically excluded on the basis of the radiological imaging data. The algorithm confidence at a position can be in particular the confidence score with which the abnormality of the examination region can be automatically excluded by the abnormality detection algorithm at this position.

The examination region can include in particular an anatomical structure. The anatomical structure can be in particular an anatomical structure of an examination object and/or an organ. The examination object can be for example a human, an animal or a phantom. The examination region can be for example a thorax.

The abnormality of the examination region can be for example radiological and/or pathological. The abnormality of the examination region can be for example an abnormality of the examination region of the anatomical structure. The abnormality of the examination region can relate to for example a shape of the anatomical structure and/or a function of the anatomical structure.

The calculation of the radiological visualization data can be effected for example by applying a visualization data calculation algorithm to the radiological imaging data and the confidence data. The radiological visualization data can be calculated in particular such that a visual evaluation of the radiological visualization data for the purpose of excluding the abnormality of the examination region requires less effort than a visual evaluation of the radiological imaging data.

The radiological visualization data can be calculated for example by firstly adapting image processing parameters as a function of the confidence data and then calculating the radiological visualization data on the basis of the radiological imaging data and the adapted image processing parameters.

The radiological visualization can be calculated for example by firstly calculating a plurality of radiological candidate visualization data, in particular independently of the confidence data, and then selecting the radiological visualization data from the plurality of radiological candidate visualization data as a function of the confidence data.

For example, the plurality of radiological candidate visualization data can comprise a tomographic series of sectional images having a slice thickness of 1 mm and a tomographic series of sectional images having a slice thickness of 5 mm. If the confidence score with which an abnormality of the examination region can be automatically excluded is sufficiently high, the tomographic series of sectional images having a slice thickness of 5 mm is selected for the radiological visualization data. The radiological candidate visualization data of the plurality of radiological candidate visualization data can be for example generated only temporarily and/or deleted again immediately after selecting the radiological visualization data from the plurality of radiological candidate visualization data.

The data reduction of the radiological visualization data relative to the radiological imaging data can be based in particular on a reduction of a dataset that must be visually evaluated, in particular by radiology staff, in order to exclude the abnormality of the examination region.

It is thus possible to reduce the effort required for a visual evaluation. The visual evaluation can be essentially limited to the verification of the results that are determined automatically by the abnormality detection algorithm in the form of the radiological visualization data. In this case, higher confidence scores result in a greater data reduction. Therefore the more reliably the abnormality of the examination region can be automatically excluded, the less data has to be visually checked for the purpose of verification.

An embodiment provides for the examination region to have a first subregion and a second subregion. In particular, provision can be made for the confidence data to relate to a confidence score with which the abnormality of the examination region in the first subregion can be automatically excluded, in particular is automatically excluded, and a confidence score with which the abnormality of the examination region in the second subregion can be automatically excluded, in particular is automatically excluded.

In particular, provision can be made for the radiological visualization data to be calculated in such a way that the data reduction in the first subregion is greater than in the second subregion specifically if the confidence score with which the abnormality of the examination region in the first subregion can be automatically excluded, in particular is automatically excluded, is greater than the confidence score with which the abnormality of the examination region in the second subregion can be automatically excluded, in particular is automatically excluded.

In particular, the confidence data can be spatially resolved. In particular, provision can be made for the confidence data to relate to the confidence score with which the abnormality of the examination region can be automatically excluded, the confidence data assigning to each position of a plurality of positions in the examination region a respective probability with which the abnormality of the examination region is truly not present at this position. In particular, provision can be made for the confidence data to relate to the confidence score with which the abnormality of the examination region can be automatically excluded, the confidence data assigning to each position of a plurality of positions in the examination region a respective probability with which the abnormality of the examination region is truly present at this position.

The abnormality detection algorithm can be designed in particular to calculate, for each position of a plurality of positions in the examination region, the probability with which the abnormality of the examination region is truly not present at this position, and/or the probability with which the abnormality of the examination region is truly present at this position, on the basis of the radiological imaging data.

An embodiment provides for the data reduction to be based on a reduction of a spatial resolution of the radiological visualization data relative to a spatial resolution of the radiological imaging data. In particular, provision can be made for the radiological visualization data to be calculated in such a way that the reduction of the spatial resolution in the first subregion is greater than in the second subregion specifically if the confidence score with which the abnormality of the examination region in the first subregion can be automatically excluded, in particular is automatically excluded, is greater than the confidence score with which the abnormality of the examination region in the second subregion can be automatically excluded, in particular is automatically excluded.

The spatial resolution can relate in particular to a voxel size, a matrix size and/or a slice thickness.

Furthermore, provision can be made for the data reduction to be based on a reduction of a contrast resolution of the radiological visualization data relative to a contrast resolution of the radiological imaging data.

An embodiment provides for the data reduction to be based on an increase of slice thickness of tomographic sectional images which are contained in the radiological visualization data relative to corresponding tomographic sectional images which are contained in the radiological imaging data.

In particular, provision can be made for the radiological visualization data to be calculated in such a way that the increase of slice thickness of tomographic sectional images of the first subregion, which images are contained in the radiological visualization data, relative to corresponding tomographic sectional images of the first subregion, which images are contained in the radiological imaging data, is greater than the increase of slice thickness of tomographic sectional images of the second subregion, which images are contained in the radiological visualization data, relative to corresponding tomographic sectional images of the second subregion, which images are contained in the radiological imaging data, specifically if the confidence score with which the abnormality of the examination region in the first subregion can be automatically excluded, in particular is automatically excluded, is greater than the confidence score with which the abnormality of the examination region in the second subregion can be automatically excluded, in particular is automatically excluded.

In particular, provision can be made such that if the confidence score with which the abnormality of the examination region can be automatically excluded exceeds a first threshold value, a slice thickness of the tomographic sectional images which are contained in the radiological visualization data is equal to a first visualization slice-thickness value, the first visualization slice-thickness value being greater than a slice thickness of the corresponding tomographic sectional images which are contained in the radiological imaging data.

In particular, provision can be made such that if the confidence score with which the abnormality of the examination region can be automatically excluded exceeds a second threshold value, a slice thickness of the tomographic sectional images which are contained in the radiological visualization data is equal to a second visualization slice-thickness value, the second visualization slice-thickness value being greater than the first visualization slice-thickness.

The slice thickness of the corresponding tomographic sectional images which are contained in the radiological imaging data can be equal to 1 mm, for example. The first visualization slice-thickness value can be equal to 3 mm and/or the second visualization slice-thickness value equal to 5 mm, for example. The effort required for a visual evaluation can therefore be reduced to a third or a fifth while retaining the ability to identify gross errors during the calculation.

The increase of slice thickness can be applied uniformly over a complete series of images, for example, or vary spatially according to the algorithm confidence. It is therefore possible in particular for selected sections of a series of images to be changed to have greater slice thicknesses according to spatial variations in the algorithm confidence.

An embodiment provides for the data reduction to be based on the fact that, instead of a three-dimensional image data set which is contained in the radiological imaging data, the radiological visualization data contains a two-dimensional projection image which is based on the three-dimensional image data set.

The three-dimensional image data set can comprise for example a plurality of tomographic sectional images. The projection image can be for example a virtual radioscopy image and/or reconstructed, in particular digitally, on the basis of a superimposition of the tomographic sectional images from the plurality of tomographic sectional images. The projection image can be for example a maximum intensity projection image and/or calculated by applying a maximum intensity projection onto the three-dimensional image data set.

An embodiment provides for the radiological imaging data to relate to the examination region in a first time segment and in a second time segment. In particular, provision can be made for the confidence data to relate to a confidence score with which the abnormality of the examination region in the first time segment can be automatically excluded, in particular is automatically excluded, and a confidence score with which the abnormality of the examination region in the second time segment can be automatically excluded, in particular is automatically excluded.

In particular, provision can be made for the radiological visualization data to relate to the examination region in the first time segment and in the second time segment, said radiological visualization data being calculated in such a way that the data reduction in the first time segment is greater than in the second time segment specifically if the confidence score with which the abnormality of the examination region in the first time segment can be automatically excluded, in particular is automatically excluded, is greater than the confidence score with which the abnormality of the examination region in the second time segment can be automatically excluded, in particular is automatically excluded.

In particular, provision can be made for both the radiological imaging data and the radiological visualization data to have a temporal dimension. In particular, provision can be made for the first time segment to be a first time segment of the radiological imaging examination of the examination region and for the second time segment to be a second time segment of the radiological imaging examination of the examination region.

The first time segment can relate for example to a first contrast medium phase of a radiological imaging examination that is supported by a contrast medium. The second time segment can relate for example to a second contrast medium phase of the radiological imaging examination that is supported by a contrast medium. Contrast medium phases of the radiological imaging examination that is supported by a contrast medium can be for example native, early arterial, late arterial, hepatic, nephrotic or urographic.

An embodiment provides for the data reduction to be based on a reduction of a temporal resolution of the radiological visualization data relative to a temporal resolution of the radiological imaging data. In particular, provision can be made for the radiological visualization data to be calculated in such a way that the reduction of the temporal resolution in the first time segment is greater than in the second time segment specifically if the confidence score with which the abnormality of the examination region in the first time segment can be automatically excluded, in particular is automatically excluded, is greater than the confidence score with which the abnormality of the examination region in the second time segment can be automatically excluded, in particular is automatically excluded.

An embodiment provides for the data reduction to be based on an increase of the sampling interval of a time series of radiological snapshots, which series is contained in the radiological visualization data, relative to a corresponding time series of radiological snapshots, which series is contained in the radiological imaging data.

In particular, provision can be made for the radiological visualization data to be calculated in such a way that the increase of the sampling interval of a time series of radiological snapshots from the first time segment, which series is contained in the radiological visualization data, relative to a corresponding time series of radiological snapshots from the first time segment, which series is contained in the radiological imaging data, is greater than the increase of the sampling interval of a time series of radiological snapshots from the second time segment, which series is contained in the radiological visualization data, relative to a corresponding time series of radiological snapshots from the second time segment, which series is contained in the radiological imaging data, specifically if the confidence score with which the abnormality of the examination region in the first time segment can be automatically excluded, in particular is automatically excluded, is greater than the confidence score with which the abnormality of the examination region in the second time segment can be automatically excluded, in particular is automatically excluded.

Via the time series of radiological snapshots, it is possible to depict in a temporally resolved manner, for example a flow of contrast medium in the examination region during a radiological imaging examination that is supported by a contrast medium.

In particular, provision can be made for each radiological snapshot in the time series of radiological snapshots to be assigned to an examination time point of the radiological imaging examination of the examination region, in particular assigned in such a way that this radiological snapshot depicts the state of the examination region at this examination time point. Two adjacent examination time points of this type delimit a corresponding sampling interval in each case.

In particular, the increase of the sampling interval can be effected in such a way that examination time points which are each assigned a radiological snapshot from the time series of radiological snapshots contained in the radiological visualization data are distributed less densely than examination time points which are each assigned a radiological snapshot from the time series of radiological snapshots contained in the radiological imaging data.

An embodiment provides for the radiological imaging data to comprise a first series of images and a second series of images. In particular, provision can be made for the confidence data to relate to a confidence score with which the abnormality of the examination region in the first series of images can be automatically excluded, in particular is automatically excluded, and a confidence score with which the abnormality of the examination region in the second series of images can be automatically excluded, in particular is automatically excluded.

In particular, provision can be made for the radiological visualization data to be calculated in such a way that the first series of images is more significantly affected by the data reduction than the second series of images specifically if the confidence score with which the abnormality of the examination region in the first series of images can be automatically excluded, in particular is automatically excluded, is greater than the confidence score with which the abnormality of the examination region in the second series of images can be automatically excluded, in particular is automatically excluded.

In particular, provision can be made for the radiological visualization data to be calculated in such a way that the radiological visualization data does not comprise the first series of images and does comprise the second series of images specifically if the confidence score with which the abnormality of the examination region in the first series of images can be automatically excluded, in particular is automatically excluded, is greater than the confidence score with which the abnormality of the examination region in the second series of images can be automatically excluded, in particular is automatically excluded.

In particular, provision can be made for the data reduction to be based on the fact that, instead of a set of series of images which is contained in the radiological imaging data, the radiological visualization data contains a proper subset of the set of series of images.

The first series of images can be for example a first image stack of tomographic sectional images. The second series of images can be for example a second image stack of tomographic sectional images. Series of images can be axial, coronal or sagittal, for example.

An embodiment provides for the radiological imaging data to comprise a first grayscale windowing and a second grayscale windowing. In particular, provision can be made for the confidence data to relate to a confidence score with which the abnormality of the examination region in the first grayscale windowing can be automatically excluded, in particular is automatically excluded, and a confidence score with which the abnormality of the examination region in the second grayscale windowing can be automatically excluded, in particular is automatically excluded.

In particular, provision can be made for the radiological visualization data to be calculated in such a way that the first grayscale windowing is more significantly affected by the data reduction than the second grayscale windowing specifically if the confidence score with which the abnormality of the examination region in the first grayscale windowing can be automatically excluded, in particular is automatically excluded, is greater than the confidence score with which the abnormality of the examination region in the second grayscale windowing can be automatically excluded, in particular is automatically excluded.

In particular, provision can be made for the radiological visualization data to be calculated in such a way that the radiological visualization data does not comprise the first grayscale windowing and does comprise the second grayscale windowing specifically if the confidence score with which the abnormality of the examination region in the first grayscale windowing can be automatically excluded, in particular is automatically excluded, is greater than the confidence score with which the abnormality of the examination region in the second grayscale windowing can be automatically excluded, in particular is automatically excluded.

In particular, provision can be made for the data reduction to be based on the fact that, instead of a set of grayscale windowings which is contained in the radiological imaging data, the radiological visualization data contains a proper subset of the set of grayscale windowings.

For example, the set of grayscale windowings which is contained in the radiological imaging data can contain a soft tissue window and a bone window, while the radiological visualization data contains only the soft tissue window and not the bone window if the abnormality detection algorithm is sure that an abnormality of the examination region in the form of bony lesions can be automatically excluded.

An embodiment provides for the radiological imaging data to relate to a first spectral range and a second spectral range. In particular, provision can be made for the confidence data to relate to a confidence score with which the abnormality of the examination region in the first spectral range can be automatically excluded, in particular is automatically excluded, and a confidence score with which the abnormality of the examination region in the second spectral range can be automatically excluded, in particular is automatically excluded.

In particular, provision can be made for the radiological visualization data to be calculated in such a way that the data reduction is greater in the first spectral range than in the second spectral range specifically if the confidence score with which the abnormality of the examination region in the first spectral range can be automatically excluded, in particular is automatically excluded, is greater than the confidence score with which the abnormality of the examination region in the second spectral range can be automatically excluded, in particular is automatically excluded.

An embodiment provides for the data reduction to be based on a reduction of a spectral resolution of the radiological visualization data relative to a spectral resolution of the radiological imaging data. In particular, provision can be made for the radiological imaging data and the radiological visualization data to each have a spectral dimension.

An embodiment provides for the data reduction to be based on the fact that, instead of a plurality of spectrally differing series of images, which series are contained in the radiological imaging data, the radiological visualization data contains a resulting series of images which is based on the plurality of spectrally differing series of images. In particular, provision can be made for the resulting series of images to be selected from the group of series of images consisting of an iodine map series of images, a virtual non-contrast series of images, a virtual non-calcium series of images and a virtual monoenergetic series of images.

Furthermore, provision can also be made for the data reduction within the resulting series of images to be effected as a function of the confidence data.

Spectrally differing series of images can be generated for example via spectral radiological imaging, in particular via spectral computed tomography. Spectral computed tomography can be for example dual-source computed tomography and/or photon-counting computed tomography and/or effected on the basis of a plurality of x-ray filters and/or a plurality of x-ray tube voltages.

The plurality of spectrally differing series of images can contain for example, for each energy level of a plurality of energy levels of a photon-counting detector, a series of images that was captured within the respective energy level. The plurality of energy levels of the photon-counting detector can comprise for example four different energy levels.

In particular, the resulting series of images can be selected from the group of series of images as a function of the confidence data. In particular, provision can be made such that each series of images from the group of series of images can be calculated via a weighted combination of at least two spectrally differing series of images from the plurality of spectrally differing series of images, for example in the form of a material decomposition. In particular, an energy for which the virtual monoenergetic series of images is calculated can be selected as a function of the confidence data.

An embodiment provides for the calculation of the confidence data to be effected by applying a trained function for abnormality detection to the radiological imaging data.

The trained function for abnormality detection can be in particular the abnormality detection algorithm and/or trained to classify the examination region and/or subregions of the examination region as normal or as anomalous on the basis of the radiological imaging data, in particular on the basis of the confidence score with which the abnormality of the examination region can be automatically excluded, in particular for a subregion of the examination region.

In particular, provision can be made for the examination region to be classified as normal by the trained function if the confidence score with which the abnormality of the examination region can be automatically excluded for the entire examination region exceeds a classification threshold value, and/or for the examination region to be classified as anomalous by the trained function if the confidence score with which the abnormality of the examination region can be automatically excluded for the entire examination region is less than the classification threshold value.

In particular, provision can be made for the subregion of the examination region to be classified as normal by the trained function if the confidence score with which the abnormality of the examination region can be automatically excluded for the subregion of the examination region exceeds a classification threshold value, and/or for the subregion of the examination region to be classified as anomalous by the trained function if the confidence score with which the abnormality of the examination region can be automatically excluded for the subregion of the examination region is less than the classification threshold value.

In particular, provision can be made for a value range for the confidence score to comprise the set of all numbers between 0 and 1, where the endpoints 0 and 1 are included. For example, the classification threshold value can be equal to 0.5, 0.7, 0.9, 0.99 or 0.999.

The function for abnormality detection can be trained for example on the basis of a set of abnormality detection training data pairs, each abnormality detection training data pair in the set of abnormality detection training data pairs comprising radiological training imaging data as training data input and corresponding abnormality detection data which was generated for example on the basis of the radiological training imaging data of radiology staff, in particular as a result of manual annotation. The confidence data can be calculated for example on the basis of a statistical model and/or on the basis of a machine learning model.

An embodiment provides for the calculation of the radiological visualization data to be effected by applying a trained function for calculating visualization data to the radiological imaging data and the confidence data.

In particular, the trained function for calculating visualization data can be the visualization data calculation algorithm and/or be trained to classify, on the basis of the radiological imaging data, image information as relevant or as irrelevant for an exclusion of the abnormality of the examination region via visual evaluation. In particular, the image information that is classified as relevant can form the radiological visualization data.

The function for calculating visualization data can be trained for example on the basis of a set of visualization training data pairs, each visualization training data pair in the set of visualization training data pairs comprising radiological training imaging data and corresponding confidence data as training data input, and corresponding radiological training visualization data as training data output.

The radiological training visualization data can be generated for example on the basis of the radiological training imaging data of radiology staff, in particular as a result of manual selection from a plurality of radiological candidate visualization data in a visualization application.

One or more example embodiments of the present invention further relates to a data processing system for providing radiological visualization data, said data processing system being designed to execute the inventive method.

The data processing system can have in particular a data interface in order to receive and/or provide data. The data processing system can have in particular a data processor in order to process data, in particular to determine, calculate and/or generate data. The data processor can be connected to a data store, for example via the data interface. The data interface can be designed for example to write data to the data store and/or read data from the data store.

One or more example embodiments of the present invention further relates to a medical imaging device having the inventive data processing system and being designed to generate the radiological imaging data. The medical imaging device can be designed in particular for a radiological imaging examination of the examination region.

The medical imaging device can be selected for example from the group of imaging modalities consisting of an x-ray device, a C-arm x-ray device, a computed tomography device (CT device), a molecular imaging device (MI device), a single-photon emission computed tomography device (SPECT device), a positron emission tomography device (PET device), a magnetic resonance tomography device (MR device), an ultrasound imaging device and combinations thereof, in particular a PET-CT device and a PET-MR device. The medical imaging device can also have a combination of an imaging modality which is selected for example from the group of imaging modalities and an irradiation modality. In this case, the irradiation modality can have for example an irradiation unit for therapeutic irradiation.

One or more example embodiments of the present invention further relates to a computer program product comprising commands which cause a computer to execute the inventive method when the commands are executed by the computer.

One or more example embodiments of the present invention further relates to a computer-readable medium comprising commands which cause a computer to execute the inventive method when the commands are executed by the computer.

The computer program product can be for example a computer program or at least one additional element in addition to the computer program. The at least one additional element of the computer program product can take the form of hardware and/or software.

The computer program product can comprise for example a storage medium, on which at least part of the computer program product is stored, and/or a key for authentication of a user of the computer program product, in particular in the form of a dongle. The computer program product and/or the computer program can comprise for example a cloud application program which is designed to distribute the commands to various processing units, in particular various computers, of a cloud computing system, each of said processing units being designed to execute one or more of the commands.

The computer-readable medium can be used to store for example the computer program product according to one of the embodiments disclosed in this application, and/or the computer program according to one of the embodiments disclosed in this application. The computer-readable medium can be for example a memory stick, a hard disk or other data medium which can be separably connected to a computer or permanently integrated in a computer. The computer-readable medium can for example form one region of a storage system.

The data processing system can comprise for example one or more components in the form of hardware and/or one or more components in the form of software. The data processing system can be composed at least partially of a computer and/or a cloud computing system, for example. The data processing system can comprise for example a cloud computing system, a computer network, a computer, a tablet computer, smartphone or similar, or a combination thereof.

The hardware can for example interact with software and/or be configurable via software. The software can be executed for example via the hardware. The hardware can be for example a storage system, an FPGA system (field-programmable gate array), an ASIC system (application-specific integrated circuit), a microcontroller system, a processor system and combinations thereof. The processor system have for example a microprocessor and/or a plurality of interacting microprocessors.

Data processing steps of the method can be executed for example in the data processor, in particular in the form of calculations. A calculation can be effected in particular by applying an algorithm, for example in the form of a trained function, to the data on which the calculation is based.

Data, in particular the radiological imaging data, can be received for example by receiving a signal which carries the data and/or by reading in the data, in particular from a data store. Data, in particular the radiological visualization data, can be provided for example by transmitting a signal which carries the data and/or by writing the data to a data store and/or by displaying the data on a display screen.

A trained function in the context of this application is understood to mean a function which is designed for machine learning. The trained function can be designed for example for monitored learning and/or for unmonitored learning. The trained function can be designed for example for deep learning and/or for reinforcement learning and/or for marginal space learning.

The trained function can for example be based on decision trees, a random forest, a logistical regression, a support vector machine, an artificial neural network, in particular a convolutional neural network and/or a recurrent neural network, generative adversarial networks, a kernel method, Bayesian classifiers or similar, or on combinations thereof. Calculations, in particular for the purpose of training the function, can be executed for example in the data processor, in particular in the form of calculations.

In the context of the invention, features which are described with reference to different embodiments of the invention and/or with reference to different statutory classes of claim (method, use, device, system, arrangement, etc.) can be combined to form further embodiments of the invention. For example, a claim which relates to a system can also be developed with features that are described or claimed in connection with a method, and vice versa. In this way, functional features of a method can be embodied by physical components of corresponding design. The use of the indefinite article "a" or "an" does not preclude multiple instances of the feature concerned. In the context of the present application, the expression "on the basis of" can be understood in particular in the sense of the expression "using". In particular, wording according to which a first feature is calculated (or alternatively: determined, generated, etc.) on the basis of a second feature does not preclude the first feature possibly being also calculated (or alternatively: determined, generated, etc.) on the basis of a third feature.

Figure 1:
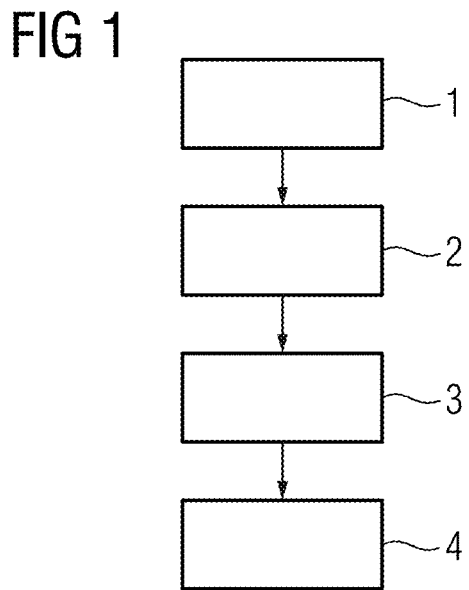
FIG. 1 shows a sequence diagram of a method for providing radiological visualization data according to one or more example embodiments.

FIG. 1 shows a sequence diagram of a method for providing radiological visualization data VD, said method comprising:

receiving 1 radiological imaging data BD which relates to an examination region U, calculating 2 confidence data KD on the basis of the radiological imaging data BD, said confidence data KD relating to a confidence score with which an abnormality of the examination region U can be automatically excluded, calculating 3 the radiological visualization data VD which relates to the examination region U, a data reduction of the radiological visualization data VD relative to the radiological imaging data BD being effected as a function of the confidence data KD, providing 4 the radiological visualization data VD.

Figure 2:
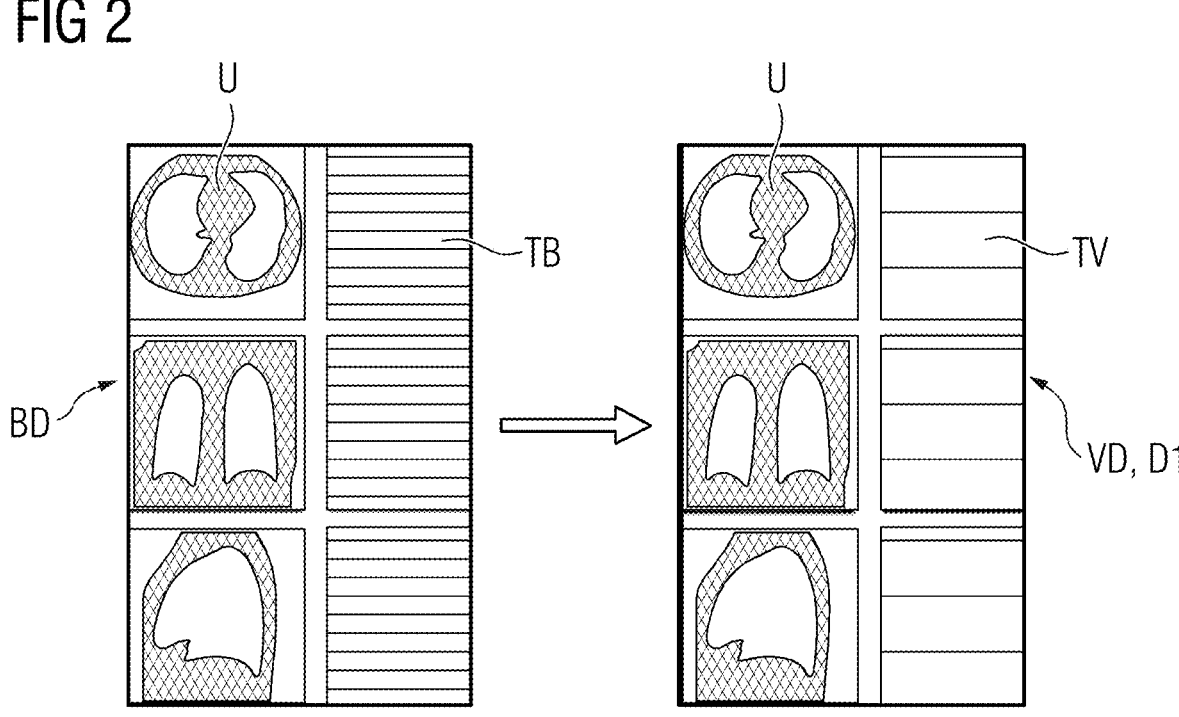
FIG. 2 shows a first example of a data reduction of the radiological visualization data relative to the radiological imaging data according to one or more example embodiments.

FIG. 2 shows a first example of a data reduction of the radiological visualization data VD relative to the radiological imaging data BD, the data reduction being based on a reduction of a spatial resolution of the radiological visualization data VD relative to a spatial resolution of the radiological imaging data BD. In this case, the data reduction is based on an increase of slice thickness of tomographic sectional images TV which are contained in the radiological visualization data VD relative to corresponding tomographic sectional images TB which are contained in the radiological imaging data BD.

Figure 3:
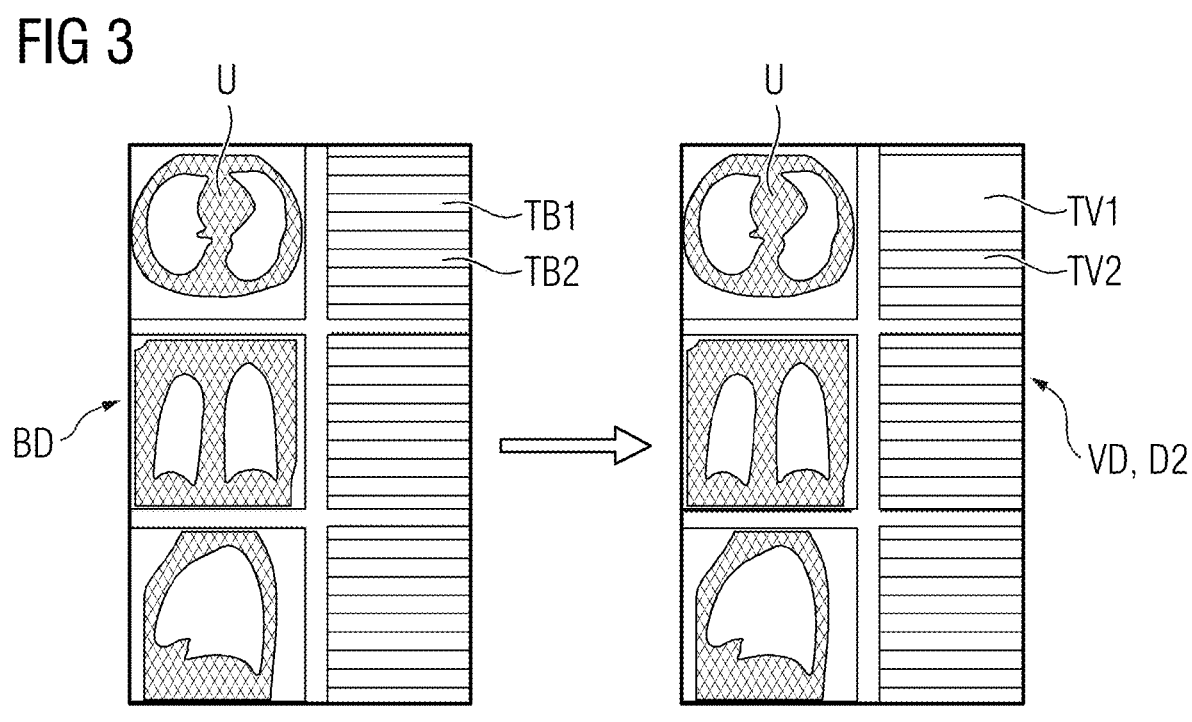
FIG. 3 shows a second example of a data reduction of the radiological visualization data relative to the radiological imaging data according to one or more example embodiments.

FIG. 3 shows a second example of a data reduction of the radiological visualization data VD relative to the radiological imaging data BD. The examination region U has a first subregion and a second subregion, the confidence data KD relating to a confidence score with which the abnormality of the examination region U in the first subregion can be automatically excluded and a confidence score with which the abnormality of the examination region U in the second subregion can be automatically excluded.

In this case, the radiological visualization data VD is calculated in such a way that the data reduction in the first subregion is greater than in the second subregion specifically if the confidence score with which the abnormality of the examination region U in the first subregion can be automatically excluded is greater than the confidence score with which the abnormality of the examination region U in the second subregion can be automatically excluded.

In this case, the radiological visualization data VD is calculated in such a way that the increase of slice thickness of tomographic sectional images TV1 of the first subregion, which images are contained in the radiological visualization data VD, relative to corresponding tomographic sectional images TB1 of the first subregion, which images are contained in the radiological imaging data BD, is greater than the increase of slice thickness of tomographic sectional images TV2 of the second subregion, which images are contained in the radiological visualization data VD, relative to corresponding tomographic sectional images TB2 of the second subregion, which images are contained in the radiological imaging data BD, specifically if the confidence score with which the abnormality of the examination region U in the first subregion can be automatically excluded is greater than the confidence score with which the abnormality of the examination region U in the second subregion can be automatically excluded.

Figure 4:
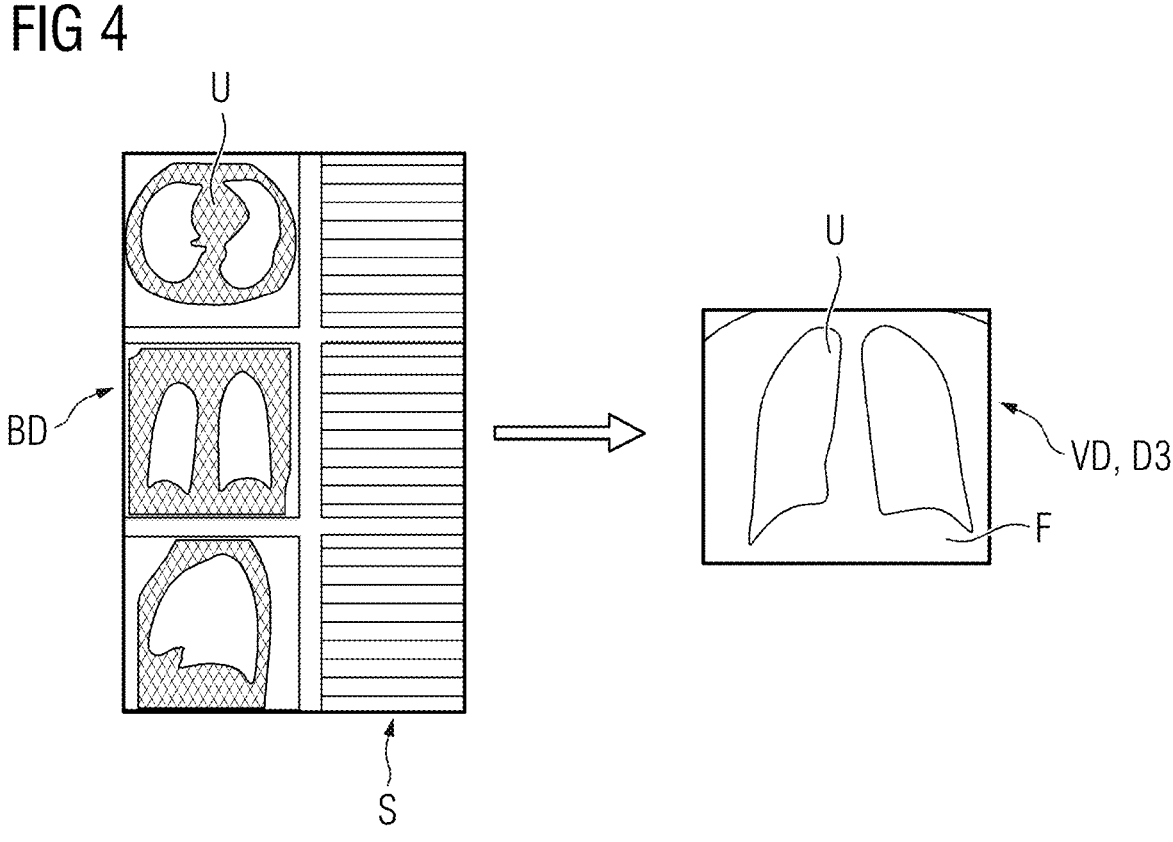
FIG. 4 shows a third example of a data reduction of the radiological visualization data relative to the radiological imaging data according to one or more example embodiments.

FIG. 4 shows a third example of a data reduction of the radiological visualization data VD relative to the radiological imaging data BD, the data reduction being based on the fact that, instead of a three-dimensional image data set S which is contained in the radiological imaging data BD, the radiological visualization data VD contains a two-dimensional projection image F which is based on the three-dimensional image data set S.

Figure 5:
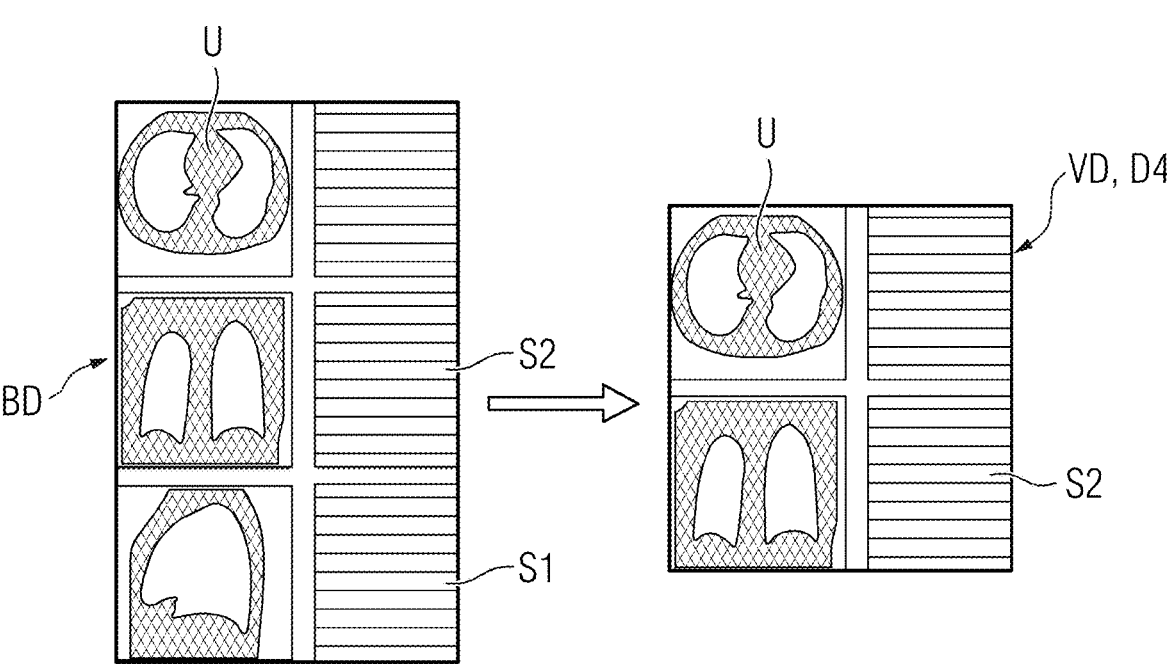
FIG. 5 shows a fourth example of a data reduction of the radiological visualization data relative to the radiological imaging data according to one or more example embodiments.

FIG. 5 shows a fourth example of a data reduction of the radiological visualization data VD relative to the radiological imaging data BD, the radiological imaging data BD comprising a first series of images S1 and a second series of images S2, the confidence data KD relating to a confidence score with which the abnormality of the examination region U in the first series of images S1 can be automatically excluded and a confidence score with which the abnormality of the examination region U in the second series of images S2 can be automatically excluded.

In this case, the radiological visualization data VD is calculated in such a way that the first series of images S1 is more significantly affected by the data reduction than the second series of images S2 specifically if the confidence score with which the abnormality of the examination region U in the first series of images S1 can be automatically excluded is greater than the confidence score with which the abnormality of the examination region U in the second series of images S2 can be automatically excluded.

In this case, the radiological visualization data VD is calculated in such a way that the radiological visualization data VD does not comprise the first series of images S1 and does comprise the second series of images S2 specifically if the confidence score with which the abnormality of the examination region U in the first series of images S1 can be automatically excluded is greater than the confidence score with which the abnormality of the examination region U in the second series of images S2 can be automatically excluded.

In this case, the data reduction is based on the fact that, instead of a set of series of images which is contained in the radiological imaging data, the radiological visualization data contains a proper subset of the set of series of images.

FIG. 6 shows an exemplary data flow diagram of the method for providing radiological visualization data VD. The calculation 2 of the confidence data KD is effected by applying the trained function A for abnormality detection to the radiological imaging data BD. The calculation 3 of the radiological visualization data VD is effected by applying a trained function V for calculating visualization data to the radiological imaging data BD and the confidence data KD. The trained function V for calculating visualization data automatically selects, on the basis of the radiological imaging data BD and the confidence data KD, at least one of the variants D1, D2, D3 and/or D4 for the radiological visualization data VD.

FIG. 7 shows the data processing system 8 for providing the radiological visualization data, said data processing system 8 being designed to execute the method in accordance with the sequence diagram shown in FIG. 1. The data processing system 8 has the data interface 8A in order to receive and/or provide data. The data processing system 8 has the data processor 8B in order to process data, in particular to determine, calculate and/or generate data.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

The invention claimed is:

1. A computer-implemented method for providing radiological visualization data, the method comprising:
receiving radiological imaging data which relates to an examination region, a first spectral range, and a second spectral range;
calculating confidence data based on the radiological imaging data, the confidence data relating to a confidence score with which an abnormality of the examination region in the first spectral range can be automatically excluded and a confidence score with which an abnormality of the examination region in the second spectral range can be automatically excluded;
calculating the radiological visualization data which relates to the examination region, wherein the radiological visualization data is based on a plurality of spectrally differing series of images of a patient, and wherein a data reduction of the radiological visualization data relative to the radiological imaging data is effected as a function of the confidence data, such that the data reduction in the first spectral range is greater than in the second spectral range specifically if the confidence score with which the abnormality of the examination region in the first spectral range can be automatically excluded is greater than the confidence score with which the abnormality of the examination region in the second spectral range can be automatically excluded; and
providing the radiological visualization data.

2. The method of claim 1, wherein
the examination region has a first subregion and a second subregion,
the confidence data relates to a confidence score with which an abnormality of the examination region in the first subregion can be automatically excluded and a confidence score with which an abnormality of the examination region in the second subregion can be automatically excluded, and
the calculating calculates the radiological visualization data such that a data reduction in the first subregion is greater than a data reduction in the second subregion if the confidence score with which the abnormality of the examination region in the first subregion can be automatically excluded is greater than the confidence score with which the abnormality of the examination region in the second subregion can be automatically excluded.

3. The method of claim 1, wherein the data reduction is based on a reduction of a spatial resolution of the radiological visualization data relative to a spatial resolution of the radiological imaging data.

4. The method of claim 1, wherein the data reduction is based on an increase of slice thickness of tomographic sectional images which are contained in the radiological visualization data relative to corresponding tomographic sectional images which are contained in the radiological imaging data.

5. The method of claim 1, wherein the radiological visualization data contains a two-dimensional projection image which is based on a three-dimensional image data set in the radiological imaging data.

6. The method of claim 1, wherein
the radiological imaging data relates to the examination region in a first time segment and in a second time segment,
the confidence data relates to a confidence score with which an abnormality of the examination region in the first time segment can be automatically excluded and a confidence score with which an abnormality of the examination region in the second time segment can be automatically excluded,
the radiological visualization data relates to the examination region in the first time segment and in the second time segment, and
the calculating calculates the radiological visualization data such that a data reduction in the first time segment is greater than a data reduction in the second time segment if the confidence score with which the abnormality of the examination region in the first time segment can be automatically excluded is greater than the confidence score with which the abnormality of the examination region in the second time segment can be automatically excluded.

7. The method of claim 1, wherein the data reduction is based on a reduction of a temporal resolution of the radiological visualization data relative to a temporal resolution of the radiological imaging data.

8. The method of claim 1, wherein the data reduction is based on an increase of a sampling interval of a time series of radiological snapshots which is contained in the radiological visualization data, relative to a corresponding time series of radiological snapshots which is contained in the radiological imaging data.

9. The method of claim 1, wherein the radiological imaging data comprises a first series of images and a second series of images, the confidence data relates to a confidence score with which an abnormality of the examination region in the first series of images can be automatically excluded and a confidence score with which an abnormality of the examination region in the second series of images can be automatically excluded, and the calculating calculates the radiological visualization data such that the first series of images is more affected by the data reduction than the second series of images if the confidence score with which the abnormality of the examination region in the first series of images can be automatically excluded is greater than the confidence score with which the abnormality of the examination region in the second series of images can be automatically excluded.

10. The method of claim 1, wherein the radiological imaging data comprises a first grayscale windowing and a second grayscale windowing, the confidence data relates to a confidence score with which an abnormality of the examination region in the first grayscale windowing can be automatically excluded and a confidence score with which an abnormality of the examination region in the second grayscale windowing can be automatically excluded, and the calculating calculates the radiological visualization data such that the first grayscale windowing is more significantly affected by the data reduction than the second grayscale windowing if the confidence score with which the abnormality of the examination region in the first grayscale windowing can be automatically excluded is greater than the confidence score with which the abnormality of the examination region in the second grayscale windowing can be automatically excluded.

11. The method of claim 1, wherein the data reduction is based on a reduction of a spectral resolution of the radiological visualization data relative to a spectral resolution of the radiological imaging data.

12. The method of claim 1, wherein the calculation of the confidence data is effected by applying a trained function for abnormality detection to the radiological imaging data.

13. The method of claim 1, wherein the calculation of the radiological visualization data is effected by applying a trained function for calculating visualization data to the radiological imaging data and the confidence data.

14. A data processing system for providing radiological visualization data, wherein the data processing system is configured to perform the method of claim 1.

15. A medical imaging device comprising:

the data processing system of claim 14, the medical imaging device being configured to generate the radiological imaging data.

16. A non-transitory computer program product comprising commands that, when executed by a computer, cause the computer to execute the method of claim 1.

17. A non-transitory computer-readable medium comprising commands that, when executed by a computer, cause the computer to execute the method of claim 1.

* * * * *